(12) United States Patent
Sakuragi et al.

(10) Patent No.: US 11,141,120 B2
(45) Date of Patent: Oct. 12, 2021

(54) RADIOGRAPHING APPARATUS

(71) Applicant: CANON KABUSHIKI KAISHA, Tokyo (JP)

(72) Inventors: Shichihei Sakuragi, Kawasaki (JP); Hidetomo Suwa, Machida (JP); Hiroto Kondo, Machida (JP); Masataka Suzuki, Yokohama (JP); Atsushi Takeuchi, Yokohama (JP); Riku Egawa, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 38 days.

(21) Appl. No.: 16/708,105

(22) Filed: Dec. 9, 2019

(65) Prior Publication Data

US 2020/0187884 A1 Jun. 18, 2020

(30) Foreign Application Priority Data

Dec. 17, 2018 (JP) .............................. JP2018-235752

(51) Int. Cl.
*A61B 6/00* (2006.01)

(52) U.S. Cl.
CPC .......... *A61B 6/4283* (2013.01); *A61B 6/4208* (2013.01)

(58) Field of Classification Search
CPC ............................ A61B 6/4283; A61B 6/4208
See application file for complete search history.

(56) References Cited

U.S. PATENT DOCUMENTS

| | | | | |
|---|---|---|---|---|
| 6,700,126 B2* | 3/2004 | Watanabe | ............. | G01T 1/2018 250/370.09 |
| 6,825,472 B2* | 11/2004 | Endo | ....................... | G01T 1/244 250/336.1 |
| 6,897,449 B1* | 5/2005 | Hata | ...................... | G01T 1/1648 250/370.09 |
| 6,967,333 B2* | 11/2005 | Hata | ....................... | G01T 1/1648 250/370.09 |
| 7,057,181 B2* | 6/2006 | Yagi | ....................... | G01T 1/2928 250/370.09 |
| 7,435,967 B2* | 10/2008 | Ertel | ..................... | G01T 1/1644 250/370.09 |

(Continued)

FOREIGN PATENT DOCUMENTS

| | | |
|---|---|---|
| JP | 2005123469 A | 5/2005 |
| JP | 4650399 B2 | 3/2011 |
| JP | 5629445 B2 | 11/2014 |

*Primary Examiner* — David P Porta
*Assistant Examiner* — Djura Malevic
(74) *Attorney, Agent, or Firm* — Canon U.S.A., Inc. I.P. Division

(57) ABSTRACT

In a radiographing apparatus, a buffer material is arranged between a support base and a side wall portion to which an incidence surface (first surface) of a casing that is positioned on an incident side of radiation R, and a back surface (second surface) of the casing that is opposite to the incidence surface are bonded, the support base is provided with a first protruding portion protruding toward the back surface, the casing is provided with a second protruding portion protruding from the back surface toward the support base, and the following relationship is satisfied:

distance $X$ < distance $Y$, where a distance between the buffer material and the support base is a distance X, and a distance between the first protruding portion of the support base and the second protruding portion of the casing is a distance Y.

11 Claims, 8 Drawing Sheets

(56) References Cited

U.S. PATENT DOCUMENTS

| | | | | |
|---|---|---|---|---|
| 7,569,831 B2* | 8/2009 | Jadrich | | G01T 1/2928 250/370.11 |
| 7,582,877 B2* | 9/2009 | Dobrusskin | | G03B 42/04 250/370.09 |
| 7,663,114 B2* | 2/2010 | Aoyagi | | G01T 1/2928 250/370.09 |
| 7,881,435 B2* | 2/2011 | Wu | | A61B 6/4405 378/98.8 |
| 7,947,960 B2* | 5/2011 | Wu | | G03B 42/02 250/370.09 |
| 8,744,044 B2* | 6/2014 | Suwa | | A61B 6/4233 378/62 |
| 9,104,097 B2* | 8/2015 | Suwa | | G03B 42/04 |
| 9,535,165 B2* | 1/2017 | Takatori | | G03B 42/04 |
| 9,978,234 B2* | 5/2018 | Kano | | A61B 6/4283 |
| 2002/0005490 A1* | 1/2002 | Watanabe | | G01T 1/2018 250/370.09 |
| 2003/0174464 A1 | 9/2003 | Funawatari et al. | | |
| 2004/0227096 A1* | 11/2004 | Yagi | | G01T 1/2928 250/370.09 |
| 2005/0017188 A1* | 1/2005 | Yagi | | G01T 1/244 250/370.09 |
| 2005/0056789 A1* | 3/2005 | Spahn | | H04N 5/321 250/370.09 |
| 2007/0138400 A1* | 6/2007 | Ertel | | G01T 1/1644 250/370.11 |
| 2007/0272873 A1* | 11/2007 | Jadrich | | G01T 1/2018 250/370.11 |
| 2008/0078940 A1* | 4/2008 | Castleberry | | G01T 1/2018 250/370.09 |
| 2009/0202038 A1 | 8/2009 | Wu et al. | | |
| 2017/0038252 A1 | 2/2017 | Suzuki et al. | | |
| 2017/0372572 A1* | 12/2017 | Kano | | C22C 23/00 |

* cited by examiner

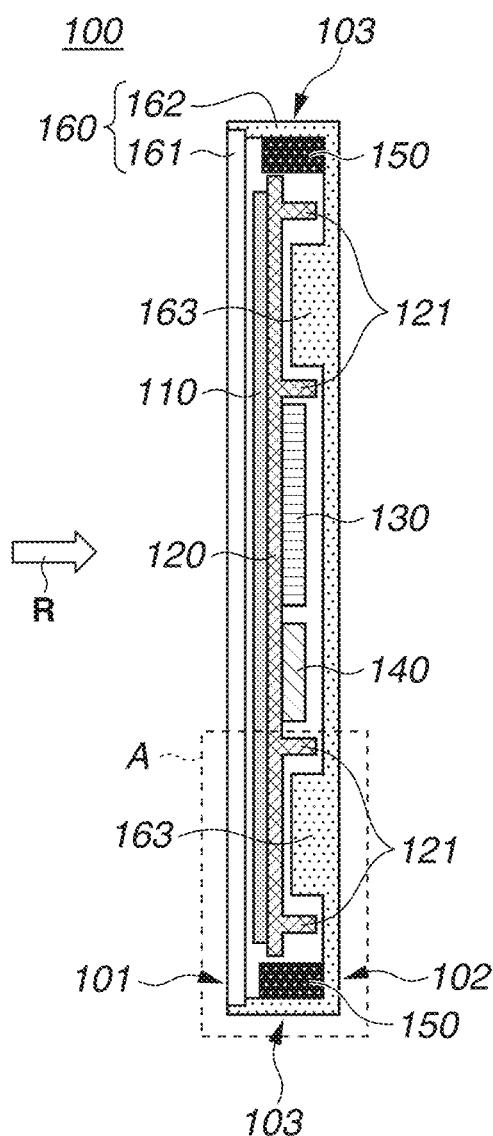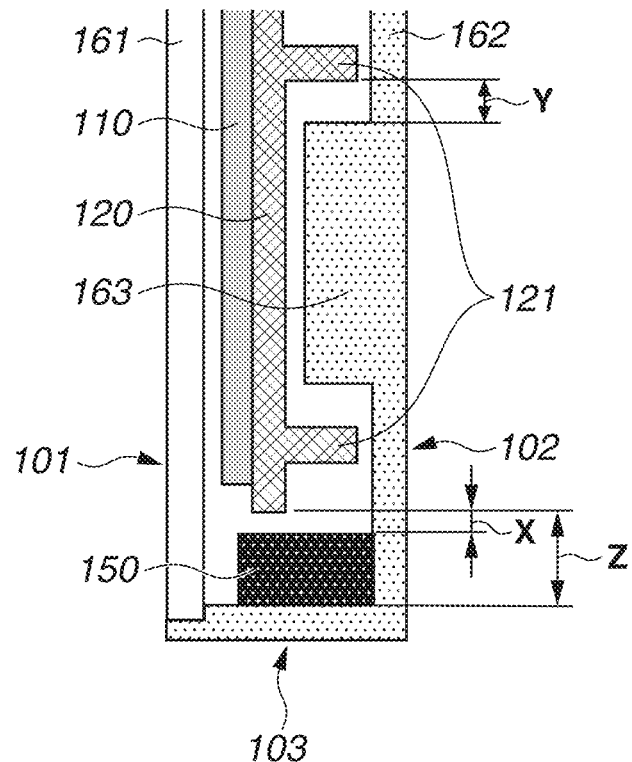

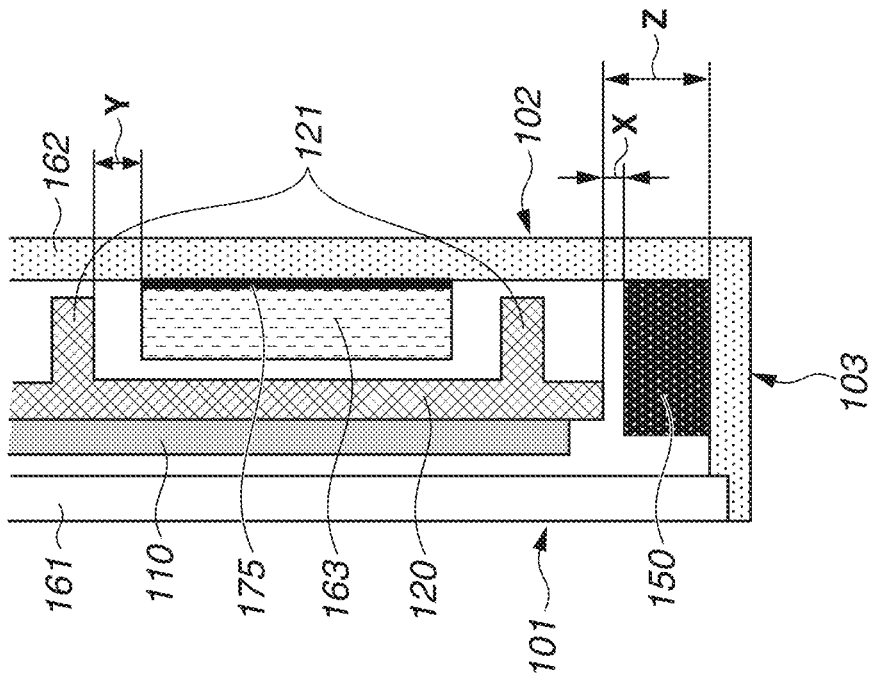
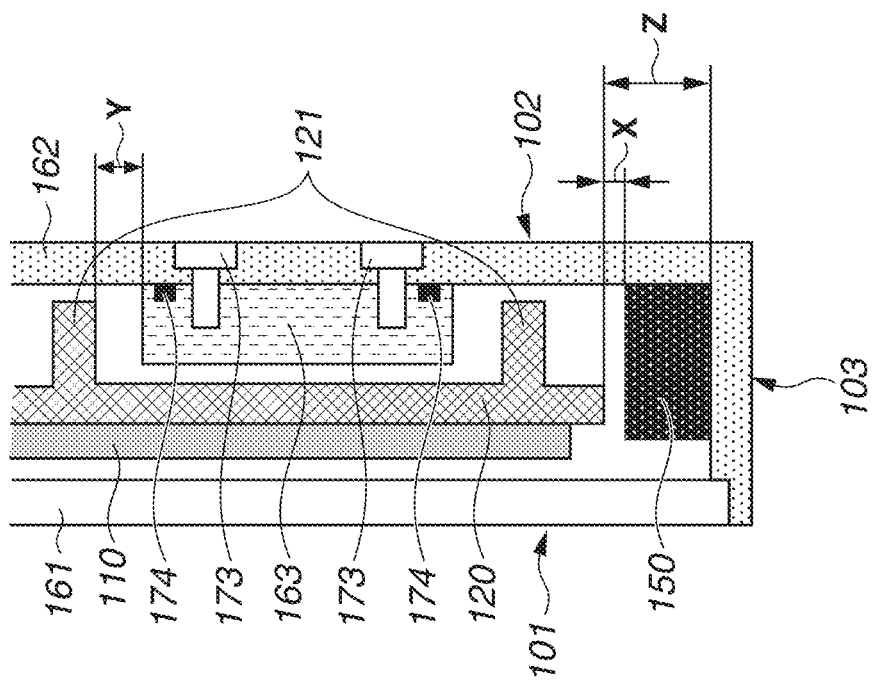

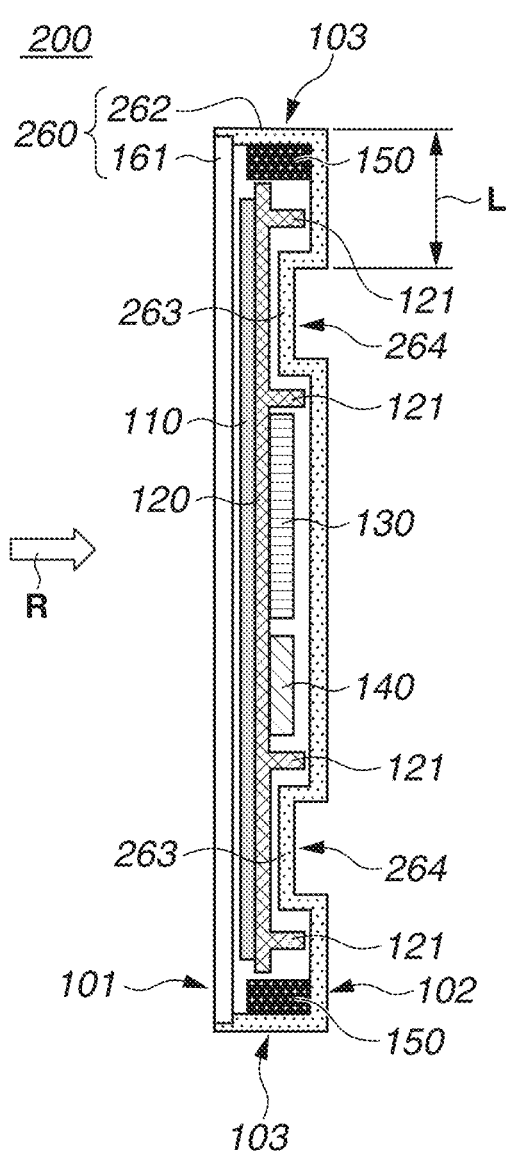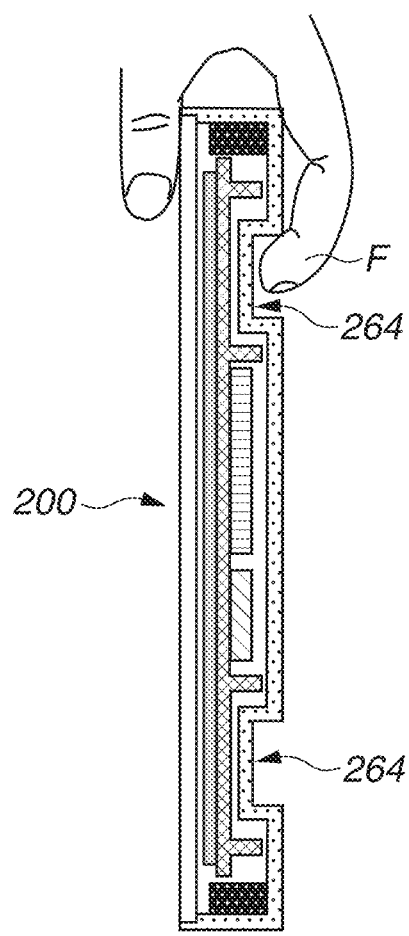

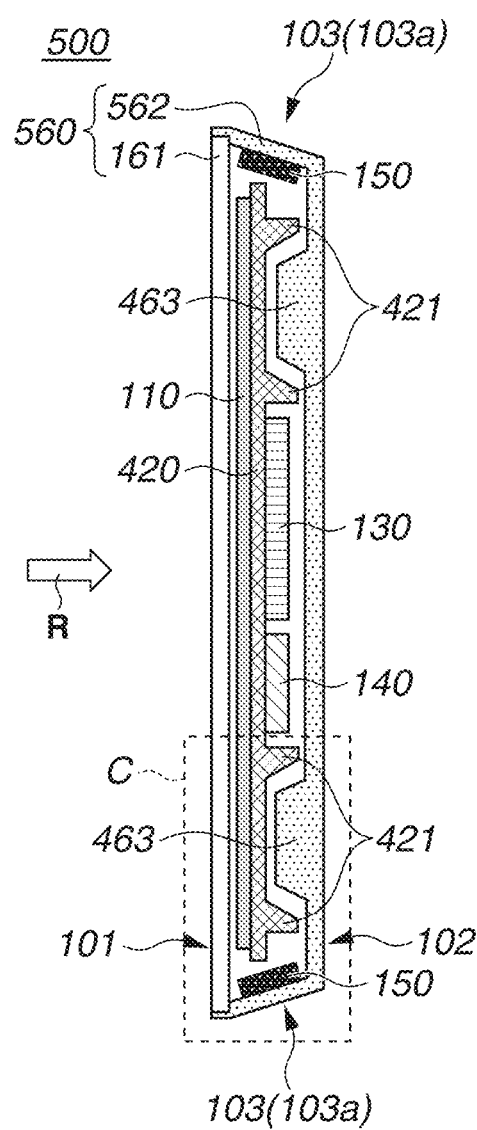
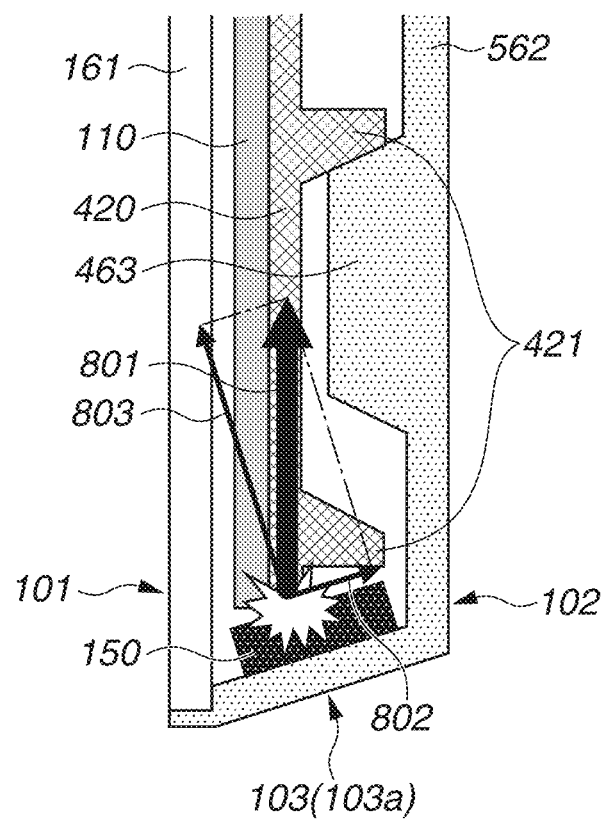

RADIOGRAPHING APPARATUS

BACKGROUND OF THE DISCLOSURE

Field of the Disclosure

The present disclosure relates to a radiographing apparatus that obtains a radiographic image by detecting incident radiation.

Description of the Related Art

In the medical field, a radiographing apparatus is widely used that emits radiation onto a subject and obtains a radiographic image based on the intensity distribution of the radiation that has passed through the subject. Nowadays, digital radiographing apparatuses have become common and such digital radiographing apparatuses have enabled digital radiographic images to be instantly obtained.

On the other hand, a lightweight thin portable radiographing apparatus is known that enables radiographing at arbitrary orientation and can be carried by a camera operator Depending on the image capturing situation, a portable radiographing apparatus is sometimes directly subjected to a load of the weight of the subject or erroneously dropped during use. For such reasons, it is desirable that the portable radiographing apparatus has a structure which eases the drop impact by absorbing or dispersing the impact in such a manner that an internal radiation detector is not damaged by the load applied from the outside or the drop impact.

Japanese Patent No. 5629445 discusses a radiographing apparatus having a structure in which a protruding portion provided on a support base supporting a radiation detector and a recess portion provided inside a casing fits into each other. This tilting structure defines a position in a planar direction of the support base in the casing, and a buffer material arranged at the fitting portion eases the impact.

Japanese Patent No. 4650399 discusses a radiographic image detector that eases the impact by arranging a buffer material between an engagement member provided on a support base and an engagement member provided on a casing.

Conventionally, a sufficiently-large thickness and a sufficiently-wide area of the buffer material have been secured to ease the impact.

In contrast to this, in the market for a portable radiographing apparatus, there is a demand that image can be captured in a large screen while enhancing portability. In other words, there is a demand that a radiation detector inside a casing has a large area and the casing needs to be thin and compact.

When handling such a demand in the market, the prior art has been insufficient from the aspect of thinning and downsizing a casing because a sufficiently-large thickness and a sufficiently-wide area of a buffer material need to be secured. In other words, in the prior art, it has been difficult to efficiently ease the drop impact in a small space inside a casing to protect a radiation detector housed in the casing, from the impact.

SUMMARY OF THE DISCLOSURE

The present disclosure is directed to efficiently easing the impact applied to the inside of a casing, and protecting a radiation detector inside the casing from the impact.

According to an aspect of the present disclosure, a radiographing apparatus includes a radiation detector configured to detect incident radiation and obtain a radiographic image, a support base configured to support the radiation detector, a buffer material, and a casing configured to house the radiation detector, the support base, and the buffer material thereinside. The buffer material is arranged between the support base and a side wall portion to which a first surface of the casing that is positioned on an incident side of the radiation, and a second surface of the casing that is opposite to the first surface are bonded, and the support base is provided with a first protruding portion protruding toward the second surface. The casing is provided with a second protruding portion protruding from the second surface toward the support base.

Further features and aspects of the present disclosure will become apparent from the following description of example embodiments with reference to the attached drawings.

BRIEF DESCRIPTION OF THE DRAWINGS

FIGS. 1A and 1B are diagrams illustrating an example of a schematic configuration of a radiographing apparatus according to a first example embodiment of the present disclosure.

FIGS. 3A and 3B illustrate a modified example of the first example embodiment of the present disclosure, and are enlarged views of a portion corresponding to the region A of the radiographing apparatus illustrated in FIG. 1A.

FIGS. 4A and 4B are diagrams illustrating an example of a schematic configuration of a radiographing apparatus according to a second example embodiment of the present disclosure.

FIGS. 8A and 8B are diagrams illustrating an example of a schematic configuration of a radiographing apparatus according to a fifth example embodiment of the present disclosure.

DESCRIPTION OF THE EMBODIMENTS

Figure 2A:
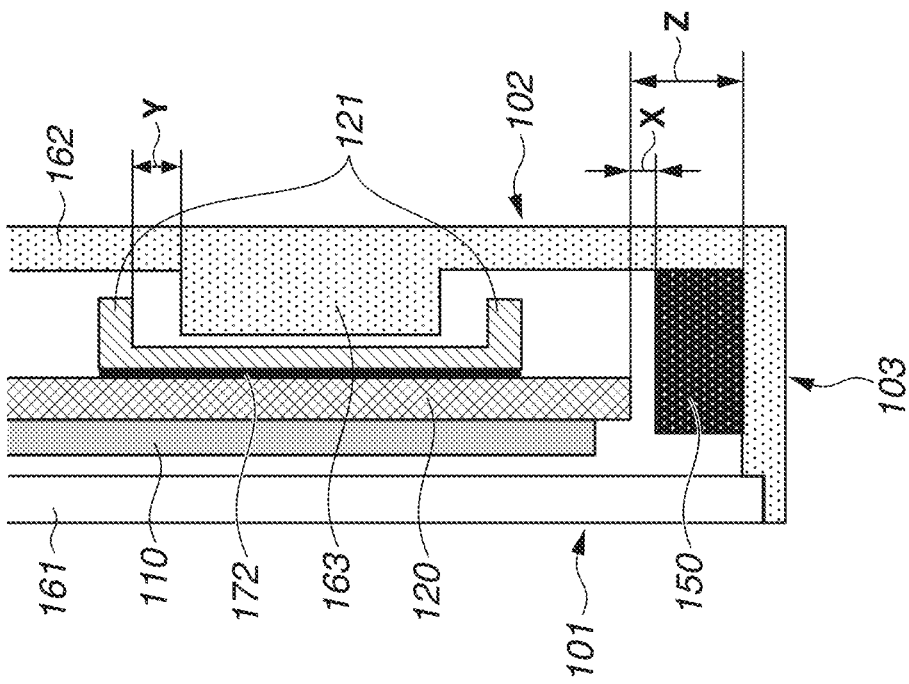
FIGS. 2A and 2B illustrate a modified example of the first example embodiment of the present disclosure, and are enlarged views of a portion corresponding to a region A of the radiographing apparatus illustrated in FIG. 1A.

Hereinafter, example embodiments of the present disclosure will be described with reference to the drawings. The following radiographing apparatuses according to the example embodiments of the present disclosure are not limited to a medical image diagnosis apparatus, and can be applied to a nondestructive inspection apparatus and an analyzing apparatus, for example. In addition, aside from alpha rays, beta rays, and gamma rays, which are beams created by particles (including photons) discharged in radioactive decay, radiation according to an example embodiment of the present disclosure includes beams having energy at a similar level or more, such as X-ray's, particle rays, and cosmic rays.

First, a first example embodiment of the present disclosure will be described.

FIGS. 1A and 1B are diagrams illustrating an example of a schematic configuration of a radiographing apparatus 100 according to the first example embodiment of the present disclosure. Specifically, FIG. 1A illustrates a cross-sectional view of the radiographing apparatus 100 in an incident direction of radiation R. In FIG. 1A, the incident direction of the radiation R is indicated by an arrow. FIG. 1B illustrates an enlarged view of a region A of the radiographing apparatus 100 illustrated in FIG. 1A.

As illustrated in FIG. 1A, the radiographing apparatus 100 includes a radiation detector 110, a support base 120, a control board 130, a battery 140, a buffer material 150, and a casing 160.

The radiation detector 110 is a component that detects the incident radiation R as an electrical signal and obtains a radiographic image.

The support base 120 is a component that supports the radiation detector 110. In the present example embodiment, the radiation detector 110 is fixed and supported by the support base 120 so as to be integrated with the support base 120.

The control board 130 is a component that controls the radiation detector 110 and performs various types of processing.

The battery 140 is a component that supplies electric energy to each component (e.g., the radiation detector 110, the control board 130, etc.) of the radiographing apparatus 100. In the present example embodiment, the radiographing apparatus 100 is driven by electric energy supplied from the battery 140. Alternatively, the radiographing apparatus 100 may be driven by electric energy supplied from the outside of the radiographing apparatus 100, for example.

The buffer material 150 is a component for easing the impact on the radiation detector 110 (further, impact on the control board 130 and the battery 140) by easing the impact on the support base 120.

The casing 160 is a component that houses the radiation detector 110, the support base 120, the control board 130, the battery 140, and the buffer material 150 thereinside. As illustrated in FIG. 1A, the casing 160 includes a top board 161 and a storage case portion 162. Specifically, the top board 161 is arranged on an incidence surface (first surface) 101 of the casing 160 that is positioned on the incident side of the radiation R. In addition, the storage case portion 162 is arranged in the casing 160 to extend from a back surface (second surface) 102 that is opposite to the incidence surface (first surface) 101, to side wall portions 103 to which the incidence surface 101 and the back surface 102 are bonded.

In the present example embodiment, the support base 120 is provided with a plurality of protruding portions 121 protruding toward the back surface 102. Furthermore, in the present example embodiment, the casing 160 (the storage case portion 162) is provided with a plurality of portions 163 protruding from the back surface 102 toward the support base 120.

In addition, in the radiographing apparatus 100 according to the present example embodiment, the radiation detector 110 detects the radiation R that has entered from the incidence surface 101, as an electrical signal, obtains a radiographic image, and outputs the radiographic image to the control board 130. The control board 130 outputs the radiographic image acquired from the radiation detector 110, to an external device by wired or wireless communication.

Next, FIG. 1B will be described.

As described above, FIG. 1B is an enlarged view of the region A of the radiographing apparatus 100 illustrated in FIG. 1A. Specifically, in the present example embodiment, as illustrated in FIG. 1B, the buffer material 150 is arranged to contact an inner side of the side wall portion 103 of the casing 160 (the storage case portion 162).

In the present example embodiment, as illustrated in FIG. 1B, a distance (of an airspace) between the buffer material 150 and the support base 120 is referred to as a distance X, and a distance (of an airspace) between the protruding portion (first protruding portion) 121 of the support base 120 and the protruding portion (second protruding portion) 163 of the casing 160 is referred to as a distance Y. Furthermore, in the present example embodiment, as illustrated in FIG. 1B, a distance between the inner side of the side wall portion 103 of the casing 160 and the support base 120 is referred to as a distance Z. In the present example embodiment, because the buffer material 150 is arranged to contact the inner side of the side wall portion 103 of the casing 160, the distance Z is obtained by adding the thickness of the buffer material 150 to the distance X. In the radiographing apparatus 100 according to the present example embodiment, the support base 120, the buffer material 150, and the casing 160 are arranged in a positional relationship satisfying distance X<distance Y<distance Z.

If a user erroneously drops the radiographing apparatus 100 including the components arranged in such a positional relationship, the casing 160 is first subjected to the drop impact. The positional relationship satisfies the distance X (the airspace between the buffer material 150 and the support base 120))<the distance Y (the airspace between the protruding portion 121 of the support base 120 and the protruding portion 163 of the casing 160). Accordingly, by the drop inertial force, the radiation detector 110 and the support base 120 initially collide with the buffer material 150. Subsequently, under the impact force, the buffer material 150 deforms in a compression direction. If the drop impact force is excessively large, the protruding portion 121 of the support base 120 contacts the protruding portion 163 of the casing 160. The contact between the protruding portion 121 of the support base 120 and the protruding portion 163 of the casing 160 prevents the radiation detector 110 and the support base 120 from dropping due to the drop inertial force. At this time, the distance X may be equal to zero. In other words, the buffer material 150 and the support base 120 may also be brought into intimate contact with each other.

The buffer material 150 is desirably an elastic member. For example, the buffer material 150 may be rubber material such as nitrile rubber, natural rubber, and silicon rubber, or an elastomer, or may be engineering plastic material such as polyoxymethylene (POM), acrylonitrile butadiene styrene (ABS), or Monocast (MC) nylon. In addition, the buffer material 150 may have, for example, a spring shape such as a plate spring or a coil spring, and may be metal material such as iron-based metal, stainless-based metal, or aluminum as long as the buffer material 150 has a spring shape.

In addition, the buffer material 150 has elasticity which absorbs the impact by getting crushed by the length of (distance Y−distance X), when the radiation detector 110 and the support base 120 collide with the buffer material 150.

Then, by the buffer material 150 absorbing the impact, even if the protruding portion 121 of the support base 120 contacts the protruding portion 163 of the casing 160, the protruding portion 121 of the support base 120 is not damaged and the support base 120 can keep supporting the radiation detector 110. In addition, a buffer material, which is not illustrated in FIG. 1, may be provided between the protruding portion 121 of the support base 120 and the protruding portion 163 of the casing 160. By providing the buffer material at the position, it becomes possible to further ease the impact applied when the protruding portion 121 of the support base 120 contacts the protruding portion 163 of the casing 160.

Furthermore, in the present example embodiment, since the positional relationship satisfies distance Y<distance Z, full crushing of the buffer material 150 does not happen, so that a buffer function is not lost. The radiation detector 110 is accordingly prevented from dropping and colliding with an inside wall of the casing 160. It, therefore, becomes possible to further ease the drop impact on the radiation detector 110.

Figure 2B:
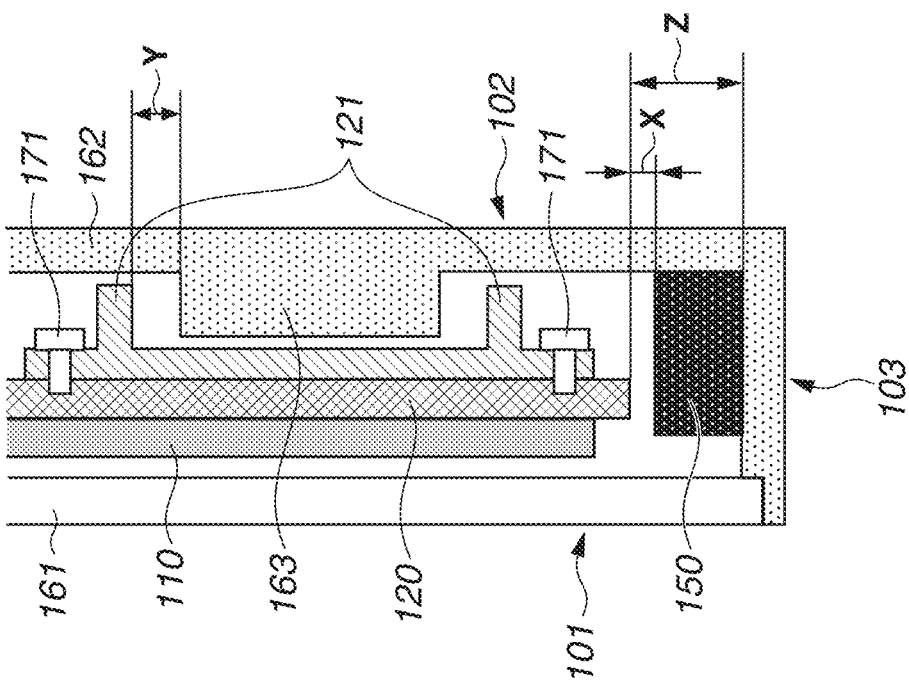

FIGS. 2A and 2B illustrate a modified example of the first example embodiment of the present disclosure, and are enlarged views of a portion corresponding to the region A of the radiographing apparatus 100 illustrated in FIG. 1A. As illustrated in FIGS. 2A and 2B, in the present example embodiment, the protruding portion 121 of the support base 120 may also be formed as a component different from the support base 120.

Specifically, FIG. 2A illustrates a configuration in which the protruding portion 121 of the support base 120, which is formed as a component different from the support base 120, is fixed to the support base 120 by the fastening using a screw 171. In addition, FIG. 2B illustrates a configuration in which the protruding portion 121 of the support base 120, which is formed as a component different from the support base 120, is attached to the support base 120 by an adhesive layer 172 made of an adhesive tape or an adhesive agent. In the present example embodiment, the configuration of the protruding portion 121 of the support base 120 is not limited to these configurations, and the protruding portion 121 may be fixed by any method as long as the protruding portion 121 remains fixed to the support base 120 even if the protruding portion 121 contacts the protruding portion 163 of the casing 160. As exemplified in FIGS. 2A and 2B, by forming the protruding portion 121 of the support base 120 as a component different from the support base 120, the protruding portion 121 of the support base 120 becomes replaceable even in a case where the protruding portion 121 is subjected to impact and damaged, for example, so that maintainability is enhanced.

Also in the configurations illustrated in FIGS. 2A and 2B, similarly to the configuration illustrated in FIG. 1B, the support base 120, the buffer material 150, and the casing 160 are arranged in the positional relationship satisfying distance X<distance Y<distance Z.

FIGS. 3A and 3B illustrate a modified example of the first example embodiment of the present disclosure, and are enlarged views of a portion corresponding to the region A of the radiographing apparatus 100 illustrated in FIG. 1A. As illustrated in FIGS. 3A and 3B, in the present example embodiment, the protruding portion 163 of the casing 160 may be formed as a component different from the casing 160 (the storage case portion 162).

Specifically, FIG. 3A illustrates a configuration in which the protruding portion 163 of the casing 160, which is formed as a component different from the storage case portion 162, is fixed to the storage case portion 162 by the fastening using a screw 173 In addition, FIG. 3B illustrates a configuration in which the protruding portion 163 of the casing 160, which is formed as a component different from the storage case portion 162, is attached to the storage case portion 162 by an adhesive layer 175 made of an adhesive tape or an adhesive agent. In the present example embodiment, the configuration of the protruding portion 163 of the casing 160 is not limited to these configurations, and the protruding portion 163 may be fixed by any method as long as the protruding portion 163 remains fixed to the storage case portion 162 in a case where the protruding portion 163 contacts the protruding portion 121 of the support base 120. As exemplified in FIGS. 3A and 3B, by forming the protruding portion 163 of the casing 160 as a component different from the casing 160 (the storage case portion 162), the protruding portion 163 of the casing 160 becomes replaceable even in a case where the protruding portion 163 is subjected to impact and damaged, for example, so that maintainability is enhanced. In addition, since it is desired in the market that the current radiographing apparatus has a waterproof property, when the protruding portion 163 of the casing 160 is formed as a component different from the casing 160 (the storage case portion 162), the apparatus needs to be sealed so as not to impair the waterproof property. For example, when the protruding portion 163 of the casing 160 is fastened to the storage case portion 162 using the screw 173 illustrated in FIG. 3A, it is desirable to provide a waterproof gasket 174 on a fastening surface at an outer position of the screw 173 as illustrated in FIG. 3A. In addition, when the protruding portion 163 of the casing 160 is attached to the storage case portion 162 by the adhesive layer 175 illustrated in FIG. 3B, the adhesive layer 175 is tightly attached without any gap, and when an adhesive tape is used, a waterproof adhesive tape is desirably used depending on the demanded waterproof level.

As described above, in the radiographing apparatus 100 according to the first example embodiment, when the distance between the buffer material 150 and the support base 120 is the distance X, and the distance between the protruding portion 121 of the support base 120 and the protruding portion 163 of the casing 160 is the distance Y, the support base 120, the buffer material 150, and the casing 160 are arranged in the positional relationship satisfying distance X<distance Y. In this configuration, for example, if the radiographing apparatus 100 is erroneously dropped in the orientation illustrated in FIG. 1A and the radiographing apparatus 100 is subjected to the impact, first, the support base 120 contacts the buffer material 150, and the protruding portion 121 of the support base 120 then contacts the protruding portion 163 of the casing 160.

In this configuration, when the radiation detector 110 housed inside the casing 160 is to be protected from the impact, it is possible to efficiently ease the impact in a small space inside the casing 160.

Furthermore, in the radiographing apparatus 100 according to the first example embodiment, if the distance between the inner side of the side wall portion 103 of the casing 160 and the support base 120 is the distance Z, the support base 120, the buffer material 150, and the casing 160 are arranged in the positional relationship satisfying distance X<distance Y<distance Z.

In this configuration, it is possible to efficiently ease the impact in a small space inside the casing 160, and moreover, it is possible to prevent a buffer function from being lost due to the fully-crushing of the buffer material 150.

Next, a second example embodiment of the present disclosure will be described. In the following description of the second example embodiment, the description of parts similar to the above-described first example embodiment will be omitted, and parts different from the above-described first example embodiment will be described.

FIGS. 4A and 4B are diagrams illustrating an example of a schematic configuration of a radiographing apparatus 200 according to the second example embodiment of the present disclosure. In FIGS. 4A and 4B, the components similar to the components illustrated in FIGS. 1A to 3B are assigned the same reference numerals, and the detailed description thereof will be omitted.

Specifically, FIG. 4A illustrates a cross-sectional view of the radiographing apparatus 200 in the incident direction of the radiation R. As illustrated in FIG. 4A, the radiographing apparatus 200 includes the radiation detector 110, the support base 120, the control board 130, the battery 140, the buffer material 150, and a casing 260.

The casing 260 is a component that houses the radiation detector 110, the support base 120, the control board 130, the battery 140, and the buffer material 150 thereinside. As illustrated in FIG. 4A, the casing 260 includes the top board 161 and a storage case portion 262. Specifically, the top board 161 is arranged on an incidence surface (first surface) 101 of the casing 260 that is positioned on the incident side of the radiation K. In addition, the storage case portion 262 is arranged so as to extend from a back surface (second surface) 102 of the casing 260 that is opposite to the incidence surface (first surface) 101, to side wall portions 103 to which the incidence surface 101 and the back surface 102 are bonded.

Similarly to the casing 160 (the storage case portion 162) in the first example embodiment, the casing 260 (the storage case portion 262) is provided with a plurality of protruding portions 263 protruding from the back surface 102 toward the support base 120. Furthermore, in the present example embodiment, in the casing 260 (the storage case portion a recess portion 264 is formed when the back surface (second surface) 102 of the casing 260 is viewed from the outside. In the example illustrated in FIG. 4A, a plurality of recess portions 264 of the casing 260 is formed on the back surface (second surface) 102 of the casing 260. In addition, each of the recess portions 264 of the casing 260 is formed in a region in which the protruding portion 263 of the casing 260 is provided, when viewed from the incident direction of the radiation R.

In this manner, by providing the recess portion 264 of the casing 260, the user can put a finger F on the recess portion 264 of the casing 260 as illustrated in FIG. 4B, for example. With this structure, the user can easily grip the radiographing apparatus 200 when carrying the radiographing apparatus 200, and it becomes possible to reduce the burdens on the user and the risk of drop of the radiographing apparatus 200.

For the user to put the finger F on the recess portion 264 of the casing 260, as illustrated in FIG. 4A, it is desirable to set a distance L from the outer side of the side wall portion 103 of the casing 260 to an end portion of the recess portion 264 of the casing 260, to fall within a range of 20 mm to 100 mm considering the length of the finger F of the user. By forming the recess portion 264 of the casing 260 within the above range, the user can unintentionally put the finger F on the recess portion 264 of the casing 260 when putting the hand on an end portion of the casing 260. Furthermore, in the recess portion 264 of the casing 260, a boundary portion in which the recess portion 264 is formed from the back surface 102 of the casing 260 may have a round (R) shape. In this manner, by forming the boundary portion to have the R shape, the user can smoothly insert the finger F into the recess portion 264 of the casing 260.

Also in the radiographing apparatus 200 according to the second example embodiment, similarly to the radiographing apparatus 100 according to the first example embodiment, the support base 120, the buffer material 150, and the casing 260 are arranged in the following positional relationship.

More specifically, when a distance between the buffer material 150 and the support base 120 is a distance X (equivalent to the distance X in FIG. 1B), and a distance between the protruding portion 121 of the support base 120 and the protruding portion 263 of the casing 260 is a distance Y (equivalent to the distance. Y in FIG. 1B), a positional relationship satisfying distance X<distance Y is obtained. Furthermore, when a distance between the inner side of the side wall portion 103 of the casing 260 and the support base 120 is a distance Z, a positional relationship satisfying distance X<distance Y<distance Z is obtained.

In addition, also in the radiographing apparatus 200 according to the second example embodiment, similarly to the radiographing apparatus 100 according to the first example embodiment, the protruding portion 121 of the support base 120 may be formed as a component different from the support base 120 as illustrated in FIGS. 2A and 2B.

As described above, in the radiographing apparatus 200 according to the second example embodiment, in addition to the positional relationship of the distances X, Y, and Z described in the first example embodiment, the recess portion 264 is formed when the back surface (second surface) 102 of the casing 260 is viewed from the outside.

With this configuration, in addition to the effects in the first example embodiment, it becomes easier for the user to grip the radiographing apparatus when carrying the radiographing apparatus, and it becomes possible to reduce the burdens on the user and the risk of drop of the radiographing apparatus.

Next, a third example embodiment of the present disclosure will be described. In the following description of the third example embodiment, the description of parts similar to the above-described first and second example embodiments will be omitted, and parts different from the above-described first and second example embodiments will be described.

Figure 5:
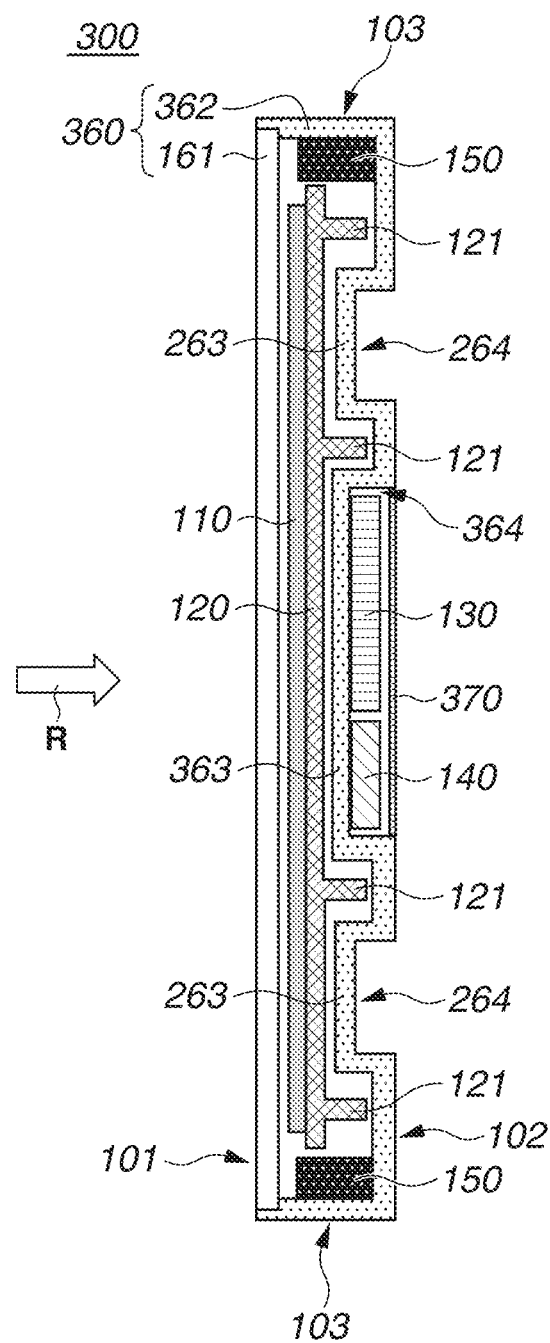
FIG. 5 is a diagram illustrating an example of a schematic configuration of a radiographing apparatus according to a third example embodiment of the present disclosure.

FIG. 5 is a diagram illustrating an example of a schematic configuration of a radiographing apparatus 300 according to the third example embodiment of the present disclosure. In FIG. 5, the components similar to the components illustrated in FIGS. 1A to 4B are assigned the same reference numerals, and the detailed description thereof will be omitted.

Specifically, FIG. 5 illustrates a cross-sectional view of the radiographing apparatus 300 in the incident direction of the radiation R. As illustrated in FIG. 5, the radiographing apparatus 300 includes the radiation detector 110, the support base 120, the control board 130, the battery 140, the buffer material 150, a casing 360, and a cover 370.

The casing 360 is a component that houses the radiation detector 110, the support base 120, and the buffer material 150 thereinside. In other words, in the present example embodiment, the casing 360 is not configured to house the control board 130 and the battery 140 thereinside. As illustrated in FIG. 5, the casing 360 includes the top board 161 and a storage case portion 362. Specifically, the top board 161 is arranged on an incidence surface (first surface) 101 of the casing 360 that is positioned on the incident side of the radiation R. In addition, the storage case portion 362 is arranged so as to extend from a back surface (second surface) 102 of the casing 360 that is opposite to the incidence surface (first surface) 101, to side wall portions 103 to which the incidence surface 101 and the back surface 102 are bonded.

Similarly to the casing 260 (the storage case portion 262) in the second example embodiment, the plurality of protruding portions 263 and the plurality of recess portions 264 are formed in the casing 360 (the storage case portion 362).

Furthermore, in the present example embodiment, in the casing 360 (the storage case portion 362), a protruding portion 363 protruding from the back surface 102 toward the support base 120 is formed, and a recess portion 364 is formed in a region in which the protruding portion 363 is provided when viewed from the incident direction of the radiation R. In the structure of the present example embodiment, the control board 130 and the battery 140 are installed on the recess portion 364 of the casing 360 (the storage case portion 362) from the outside, and the recess portion 364 is covered with the cover 370 to house the control board 130 and the battery 140. Here, the cover 370 may be attached to the casing 360 (the storage case portion 362) using an adhesive agent or a double-stick tape. Alternatively, the cover 370 may be fixed to the casing 360 (the storage case portion 362) by the fastening using a screw.

In the structures of the radiographing apparatus 100 according to the first example embodiment and the radiographing apparatus 200 according to the second example embodiment, which have been described above, it is necessary to detach the casing when the maintenance of the control board 130 or the replacement of the battery 140 is required. In contrast, in the structure of the radiographing apparatus 300 according to the present example embodiment, the maintenance of the control board 130 and a replacement work of the battery 140 can be carried out by a requisite minimum detachment work of simply removing the cover 370.

Also in the radiographing apparatus 300 according to the third example embodiment, similarly to the radiographing apparatus 100 according to the first example embodiment, the support base 120, the buffer material 150, and the casing 360 are arranged in the following positional relationship.

More specifically, when a distance between the buffer material 150 and the support base 120 is a distance X (equivalent to the distance X in FIG. 1B), and a distance between the protruding portion 121 of the support base 120 and the protruding portion 263 (furthermore, the protruding portion 363) of the casing 360 is a distance Y (equivalent to the distance Y in FIG. 1B), a positional relationship satisfying distance X<distance Y is obtained. Furthermore, when a distance between the inner side of the side wall portion 103 of the casing 360 and the support base 120 is a distance Z, a positional relationship satisfying distance X<distance Y<distance Z is obtained.

In addition, also in the radiographing apparatus 300 according to the third example embodiment, similarly to the radiographing apparatus 100 according to the first example embodiment, the protruding portion 121 of the support base 120 may be formed as a component different from the support base 120 as illustrated in FIGS. 2A and 2B.

As described above, in the radiographing apparatus 300 according to the third example embodiment, in addition to the positional relationship of the distances X, Y, and Z described in the first example embodiment, the battery 140 and the control board 130 are arranged on one recess portion 364 among the plurality of recess portions 264 and 364.

In this configuration, in addition to the effects of the first example embodiment, a radiographing apparatus superior in maintainability can be provided.

Next, a fourth example embodiment of the present disclosure will be described. In the following description of the fourth example embodiment, the description of parts similar to the above-described first to third example embodiments will be omitted, and parts different from the above-described first to third example embodiments will be described.

Figure 6A:
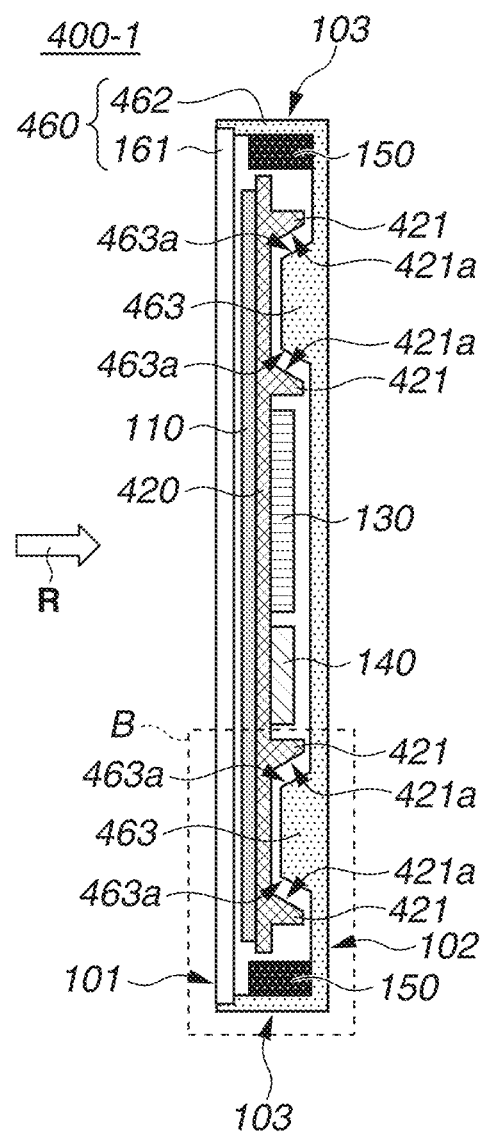
FIGS. 6A and 6B are diagrams illustrating a first example of a schematic configuration of a radiographing apparatus according to a fourth example embodiment of the present disclosure.
Figure 6B:
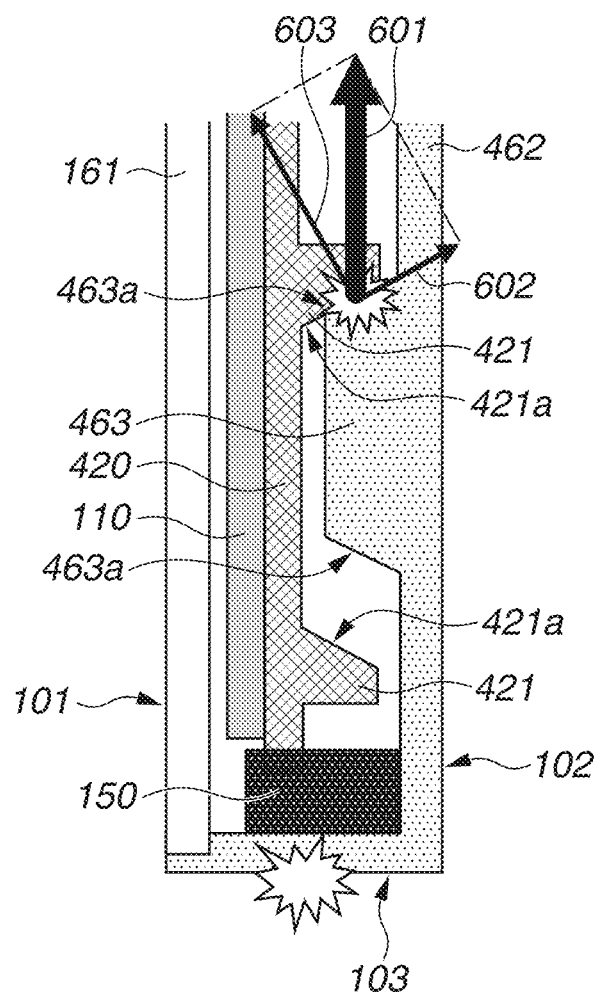

FIGS. 6A and 6B are diagrams illustrating a first example of a schematic configuration of a radiographing apparatus 400 according to the fourth example embodiment of the present disclosure. In FIGS. 6A and 6B, the components similar to the components illustrated in FIGS. 1A to 5 are assigned the same reference numerals, and the detailed description thereof will be omitted. In addition, in the following description, the radiographing apparatus 400 illustrated in FIGS. 6A and 6B is described as a "radiographing apparatus 400-1".

Specifically, FIG. 6A illustrates a cross-sectional view of the radiographing apparatus 400-1 in the incident direction of the radiation R. FIG. 6B illustrates an enlarged view of a region B of the radiographing apparatus 400-1 illustrated in FIG. 6A.

As illustrated in FIG. 6A, the radiographing apparatus 400-1 includes the radiation detector 110, a support base 420, the control board 130, the battery 140, the buffer material 150, and a casing 460.

The casing 460 is a portion that houses the radiation detector 110, the support base 420, the control board 130, the battery 140, and the buffer material 150 thereinside. As illustrated in FIG. 6A, the casing 460 includes the top board 161 and a storage case portion 462. More specifically, the top board 161 is arranged on an incidence surface (first surface) 101 of the casing 460 that is positioned on the incident side of the radiation R. In addition, the storage case portion 462 is arranged to extend from a back surface (second surface) 102 of the casing 460 that is opposite to the incidence surface (first surface) 101, to side wall portions 103 to which the incidence surface 101 and the back surface 102 are bonded.

As illustrated in FIG. 6A, the casing 460 (the storage case portion 462) is provided with a plurality of protruding portions 463 protruding from the back surface 102 toward the support base 120. Here, the protruding portion 463 of the casing 460 has a surface 463a inclined with respect to the incident direction of the radiation R.

The support base 420 is provided with a plurality of protruding portions 421 protruding toward the back surface 102. Here, the protruding portion 421 of the support base 420 has a surface 421a inclined with respect to the incident direction of the radiation R. In the present example embodiment, the inclined surface 421a of the protruding portion 421 of the support base 420 and the inclined surface 463a of the protruding portion 463 of the casing 460 are substantially parallel to each other.

Similarly to the case described in the first example embodiment, if drop impact is applied to the radiographing apparatus 400-1, first, the radiation detector 110 and the support base 420 collide with the buffer material 150. Subsequently, the buffer material 150 is subjected to the impact force and deforms in the compression direction. If the drop impact is excessively large, the protruding portion 421 of the support base 420 contacts the protruding portion 463 of the casing 460. Nevertheless, in the structure of the radiographing apparatus 400-1 according to the present example embodiment, as illustrated in FIG. 6B, impact force 601 is dispersed toward an incidence surface side 603 or a back surface side 602 along the inclined surface 421a of the protruding portion 421 of the support base 420 and the inclined surface 463a of the protruding portion 463 of the casing 460. By employing the structure of the radiographing apparatus 400-1 illustrated in FIGS. 6A and 6B, impact force applied to the radiation detector 110 and the support base 420 is further eased.

Figure 7:
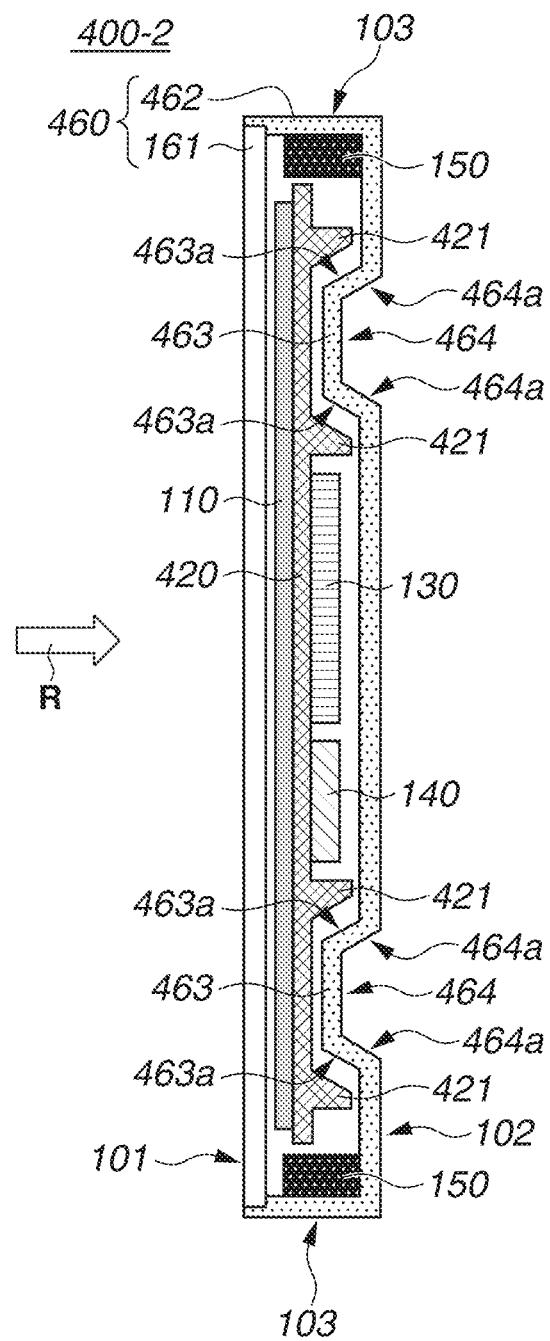
FIG. 7 is a diagram illustrating a second example of a schematic configuration of a radiographing apparatus according to the fourth example embodiment of the present disclosure.

FIG. 7 is a diagram illustrating a second example of a schematic configuration of a radiographing apparatus 400 according to the fourth example embodiment of the present disclosure. In FIG. 7, the components similar to the components illustrated in FIGS. 1A to 6B are assigned the same reference numerals, and the detailed description thereof will be omitted. In addition, in the following description, the radiographing apparatus 400 illustrated in FIG. 7 is described as a "radiographing apparatus 400-2".

Specifically, FIG. 7 illustrates a cross-sectional view of the radiographing apparatus 400-2 in the incident direction of the radiation R. In the radiographing apparatus 400-2 illustrated in FIG. 7, in addition to the components of the radiographing apparatus 400-1 illustrated in FIG. 6A, a recess portion 464 is further formed on the casing 460 (the storage case portion 462) when the back surface (second surface) 102 of the casing 460 is viewed from the outside. In addition, if the recess portion 464 is provided, as illustrated in FIG. 7, an inclined surface 464a substantially parallel to the inclined surface 463a of the protruding portion 463 of the casing 460 is provided. By providing the inclined surface 464a in the recess portion 464 of the casing 460, when the user grips the radiographing apparatus 400-2, a fingertip of the user is smoothly inserted into the recess portion 464 of the casing 460, and the user can easily grip the radiographing apparatus 400-2 in this shape.

Also in the radiographing apparatus 400 according to the fourth example embodiment, similarly to the radiographing apparatus 100 according to the first example embodiment, the support base 420, the buffer material 150, and the casing 460 are arranged in the following positional relationship.

More specifically, when a distance between the buffer material 150 and the support base 420 is a distance X (equivalent to the distance X in FIG. 1B), and a distance between the protruding portion 421 of the support base 420 and the protruding portion 463 of the casing 460 is a distance Y (equivalent to the distance. Y in FIG. 1B), a positional relationship satisfying distance X<distance Y is obtained. Furthermore, when a distance between the inner side of the side wall portion 103 of the casing 460 and the support base 420 is a distance Z, a positional relationship satisfying distance X<distance Y<distance Z is obtained.

In addition, also in the radiographing apparatus 400 according to the fourth example embodiment, similarly to the radiographing apparatus 100 according to the first example embodiment, the protruding portion 421 of the support base 420 may be formed as a component different from the support base 420 as illustrated in FIGS. 2A and 2B. Furthermore, in the radiographing apparatus 400-1 according to the fourth example embodiment, similarly to the radiographing apparatus 100 according to the first example embodiment, the protruding portion 463 of the casing 460 may be formed as a component different from the casing 460 as illustrated in FIGS. 3A and 3B. In addition, also in the radiographing apparatus 400 according to the fourth example embodiment, similarly to the radiographing apparatus 300 according to the third example embodiment, the following configuration may be employed. More specifically, the protruding portion 363 and the recess portion 364 illustrated in FIG. 5 may be provided on the casing 460 so that the control hoard 130 and the battery 140 are installed on the recess portion 364 from the outside, and the recess portion 364 is covered with the cover 370.

As described above, in the radiographing apparatus 400 according to the fourth example embodiment, in addition to the positional relationship of the distances X, Y, and Z described in the first example embodiment, the protruding portion 421 of the support base 420 and the protruding portion 463 of the casing 460 are formed to have the inclined surfaces substantially parallel to each other.

With this configuration, in addition to the effects in the first example embodiment, it is possible to further ease the impact.

Next, a fifth example embodiment of the present disclosure will be described. In the following description of the fifth example embodiment, the description of parts similar to the above-described first to fourth example embodiments will be omitted; and parts different from the above-described first to fourth example embodiments will be described.

FIGS. 8A and 8B are diagrams illustrating an example of a schematic configuration of a radiographing apparatus 500 according to the fifth example embodiment of the present disclosure. In FIGS. 8A and 8B, the components similar to the components illustrated in FIGS. 1A to 7 are assigned the same reference numerals, and the detailed description thereof will be omitted.

Specifically, FIG. 8A illustrates a cross-sectional view of the radiographing apparatus 500 in the incident direction of the radiation R. FIG. 8B illustrates an enlarged view of a region C of the radiographing apparatus 500 illustrated in FIG. 8A.

As illustrated in FIG. 8A, the radiographing apparatus 500 includes the radiation detector 110, the support base 420, the control board 130, the battery 140, the buffer material 150, and a casing 560.

The casing 560 is a portion that houses the radiation detector 110, the support base 420, the control board 130, the battery 140, and the buffer material 150 thereinside. As illustrated in FIG. 8A, the casing 560 includes the top board 161 and a storage case portion 562. Specifically, the top board 161 is arranged on an incidence surface (first surface) 101 of the casing 560 that is positioned on the incident side of the radiation R. In addition, the storage case portion 562 is arranged so as to extend from a back surface (second surface) 102 of the casing 560 that is opposite to the incidence surface (first surface) 101, to side wall portions 103 bonding the incidence surface 101 and the back surface 102.

As illustrated in FIG. 8A, the casing 560 (the storage case portion 562) is provided with the plurality of protruding portions 463 protruding from the back surface 102 toward the support base 120, which are the same as those in FIG. 6A. Similarly to FIG. 6A, the protruding portion 463 of the casing 560 has an inclined surface (the inclined surface 463a illustrated in FIG. 6A) inclined with respect to the incident direction of the radiation R. In the present example embodiment, in the casing 560 (the storage case portion 562), the side wall portion 103 of the casing 560 has an inclined surface 103a not substantially vertical to the incidence surface (first surface) 101 and the back surface (second surface) 102. In addition, in the present example embodiment, the buffer material 150 is installed so as to be substantially parallel to the inclined surface 103a of the side wall portion 103 of the casing 560.

Similarly to the case described in the first example embodiment, if drop impact is applied to the radiographing apparatus 500, first, the radiation detector 110 and the support base 420 collide with the buffer material 150. Subsequently, the buffer material 150 is subjected to the impact force and deforms in the compression direction. In the structure of the radiographing apparatus 500, as illustrated in FIG. 8B, impact force 801 is dispersed to an incidence surface side 803 or a back surface side 802 along the inclined surface 103a of the side wall portion 103 of the casing 560 and the inclined surface of the buffer material 150, By employing the structure of the radiographing apparatus 500 illustrated in FIGS. 8A and 8B, impact force applied to the radiation detector 110 and the support base 420 is further eased.

Also in the radiographing apparatus 500 according to the fifth example embodiment, similarly to the radiographing apparatus 100 according to the first example embodiment, the support base 420, the buffer material 150, and the casing 560 are arranged in the following positional relationship.

More specifically, when a distance between the buffer material 150 and the support base 420 is a distance X (equivalent to the distance X in FIG. 1B), and a distance between the protruding portion 421 of the support base 420 and the protruding portion 463 of the casing 560 is a distance Y (equivalent to the distance. Y in FIG. 1B), a positional relationship satisfying distance X<distance Y is obtained. Furthermore, when a distance between the inner side of the side wall portion 103 of the casing 560 and the support base 420 is a distance Z, a positional relationship satisfying distance X<distance Y<distance Z is obtained.

In addition, also in the radiographing apparatus 500 according to the fifth example embodiment, similarly to the radiographing apparatus 100 according to the first example embodiment, the protruding portion 421 of the support base 420 may be formed as a component different from the support base 420 as illustrated in FIGS. 2A and 2B. Furthermore, also in the radiographing apparatus 500 according to the fifth example embodiment, similarly to the radiographing apparatus 100 according to the first example embodiment, the protruding portion 463 of the casing 560 may be formed as a component different from the casing 560 as illustrated in FIGS. 3A and 3B. In addition, also in the radiographing apparatus 500 according to the fifth example embodiment, similarly to the radiographing apparatus 300 according to the third example embodiment, the following configuration may be employed. More specifically, the protruding portion 363 and the recess portion 364 illustrated in FIG. 5 may be provided on the casing 560, the control board 130 and the battery 140 may be installed on the recess portion 364 from the outside, and the recess portion 364 may be covered with the cover 370.

As described above, in the radiographing apparatus 500 according to the fifth example embodiment, in addition to the positional relationship of the distances X, Y, and Z described in the first example embodiment, the side wall portion 103 of the casing 560 has the inclined surface 103a not substantially vertical to the incidence surface (first surface) 101 and the back surface (second surface) 102.

With this configuration, in addition to the effects in the first example embodiment, it is possible to further ease the impact.

According to an example embodiment of the present disclosure, when protecting a radiation detector housed inside a casing from the impact, it is possible to efficiently ease the impact in a small space inside the casing.

While the present disclosure has been described with reference to example embodiments, it is to be understood that the disclosure is not limited to the disclosed example embodiments. The scope of the following claims is to be accorded the broadest interpretation so as to encompass all such modifications and equivalent structures and functions.

This application claims the benefit of Japanese Patent Application No. 2018-235752, filed Dec. 17, 2018, which is hereby incorporated by reference herein in its entirety.

What is claimed is:

1. A radiographing apparatus comprising:
a radiation detector configured to detect incident radiation and obtain a radiographic image;
a support base configured to support the radiation detector;
a buffer material; and
a casing configured to house the radiation detector, the support base, and the buffer material inside the casing,
wherein the buffer material is arranged between the support base and a side wall portion, to which a first surface of the casing that is positioned on an incident side of the incident radiation and a second surface of the casing that is opposite to the first surface are bonded, and the support base is provided with a first protruding portion protruding toward the second surface,
wherein the casing is provided with a second protruding portion protruding from the second surface toward the support base, and
wherein a side surface of the first protruding portion and a side surface of the second protruding portion that faces the side surface of the first protruding portion are separated at a distance in a contactable manner.

2. The radiographing apparatus according to claim 1, wherein the support base and the buffer material are separated at a distance in a contactable manner.

3. The radiographing apparatus according to claim 2, wherein the following relationship is satisfied:

$$\text{distance } X < \text{distance } Y,$$

where a distance between the support base and the buffer material is a distance X, and a distance between the first protruding portion and the second protruding portion is a distance Y.

4. The radiographing apparatus according to claim 3, wherein the following relationship is satisfied:

$$\text{distance } X < \text{distance } Y < \text{distance } Z,$$

where a distance between the support base and an inner side of the side wall portion is a distance Z.

5. The radiographing apparatus according to claim 3, wherein, when impact is applied, the support base contacts the buffer material, and then the first protruding portion contacts the second protruding portion.

6. The radiographing apparatus according to claim 1, wherein the side wall portion has an inclined surface not substantially vertical to the first surface and the second surface.

7. The radiographing apparatus according to claim 1, wherein the buffer material is an elastic member.

8. The radiographing apparatus according to claim 1, wherein the buffer material is arranged in contact with an inner side of the side wall portion.

9. A radiographing apparatus comprising:
a radiation detector configured to detect incident radiation and obtain a radiographic image;
a support base configured to support the radiation detector;
a buffer material; and
a casing configured to house the radiation detector, the support base, and the buffer material inside the casing,
wherein the buffer material is arranged between the support base and a side wall portion, to which a first surface of the casing that is positioned on an incident side of the incident radiation and a second surface of the casing that is opposite to the first surface are bonded, and the support base is provided with a first protruding portion protruding toward the second surface, wherein the casing is provided with a second protruding portion protruding from the second surface toward the support base, and wherein a recess portion is formed when the second surface of the casing is viewed from an outside, and the recess portion is formed in a region in which the second protruding portion of the casing is provided.

10. The radiographing apparatus according to claim 9, wherein a plurality of the recess portions is formed, and
wherein a battery configured to supply electric energy to the radiation detector and a control board configured to control the radiation detector are arranged on one recess portion of the plurality of recess portions.

11. A radiographing apparatus comprising:
a radiation detector configured to detect incident radiation and obtain a radiographic image;
a support base configured to support the radiation detector;
a buffer material; and
a casing configured to house the radiation detector, the support base, and the buffer material inside the casing,
wherein the buffer material is arranged between the support base and a side wall portion, to which a first surface of the casing that is positioned on an incident side of the incident radiation and a second surface of the casing that is opposite to the first surface are bonded, and the support base is provided with a first protruding portion protruding toward the second surface,
wherein the casing is provided with a second protruding portion protruding from the second surface toward the support base,
wherein the first protruding portion and the second protruding portion have inclined surfaces inclined with respect to an incident direction of the incident radiation, and
wherein the inclined surface of the first protruding portion and the inclined surface of the second protruding portion are substantially parallel to each other.

* * * * *